United States Patent

Lam

Patent Number: 4,876,375
Date of Patent: Oct. 24, 1989

[54] NORBORNYL DITHIOCARBAMATES

[75] Inventor: William Y. Lam, Ballwin, Mo.

[73] Assignee: Ethyl Petroleum Additives, Inc., St. Louis, Mo.

[21] Appl. No.: 189,101

[22] Filed: May 2, 1988

[51] Int. Cl.$^4$ ............................................. C07C 155/08
[52] U.S. Cl. ..................................... 558/235; 252/47.5
[58] Field of Search ......................... 252/47.5; 558/235

[56] References Cited

U.S. PATENT DOCUMENTS

| | | | |
|---|---|---|---|
| 2,579,384 | 12/1951 | Handy | 558/235 |
| 3,882,031 | 5/1975 | Askew et al. | 252/45 |
| 3,885,039 | 5/1975 | Pinkowski et al. | 514/479 |
| 4,501,678 | 2/1985 | Katayama et al. | 252/32.7 E |

Primary Examiner—Mary C. Lee
Assistant Examiner—Robert C. Whittenbaugh
Attorney, Agent, or Firm—David M. Bunnell

[57] ABSTRACT

Compounds having the formula:

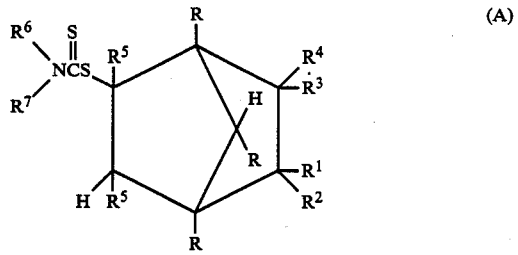

wherein:
a. each of R, $R^2$ and $R^4$ when taken singly is a hydrogen atom, an alkyl group containing from 1 to about 15 carbon atoms, an aryl group containing from 6 to about 15 carbon atoms or a cycloalkyl group containing from 4 to about 10 carbon atoms;
b. each of $R^1$ and $R^3$ when taken singly is a hydrogen atom, an alkyl group containing from 1 to about 15 carbon atoms; an aryl group containing from 6 to about 15 carbon atoms; a cycloalkyl group containing from 4 to about 10 carbon atoms or an alkenyl group containing from 2 to about 10 carbon atoms or $R^1$ and $R^3$ taken together form the group —CHYCY=CY— in which Y is a hydrogen atom or a methyl group of $R^1$ together with $R^2$ form an alkylidene group containing from 1 to about 6 carbon atoms;
c. $R^5$ is a hydrogen atom or an alkyl group containing from 1 to about 15 carbon atoms;
d. $R^6$ is an organic radical selected from an alkyl group, an alkenyl group, an aryl group or an aralkyl group in which the alkyl or alkenyl groups contain up to 32 carbon atoms and the aryl or aralkyl groups contain up to 15 carbon atoms each; and
e. $R^7$ is hydrogen or an organic radical selected from an alkyl group or alkenyl group, an aryl or aralkyl group in which the alkyl or alkenyl groups contain up to 32 carbon atoms and the aryl or aralkyl groups contain up to 15 carbon atoms each, are effective antiwear and antioxidant additives in lubricating oils.

4 Claims, No Drawings

NORBORNYL DITHIOCARBAMATES

BACKGROUND OF THE INVENTION

This invention relates to dithiocarbamyl substituted norbornyl products having utility as lubricant additives and lubricating compositions containing them. The invention also relates to a process for preparing such products.

Additives are conventionally added to lubricating oils to improve their properties. Antiwear additives used in the past include compounds such as zinc dialkyldithiophosphates, sulfurized sperm oil, and the like. Antioxidant additives used in the past include sulfurized oil-soluble organic compounds, such as wax sulfides and polysulfides, sulfurized olefins, sulfurized fatty acid esters, and sulfurized olefin esters, as well as oil-soluble phenolic and aromatic amine antioxidants.

It has now been found that certain dithiocarbamyl substituted norbornyl products are very effective antiwear and antioxidant additives in lubricating compositions such as crankcase lubricants.

DETAILED DESCRIPTION OF THE INVENTION

Accordingly, in one aspect of the present invention there is provided an antiwear and antioxidant compound having the general formula:

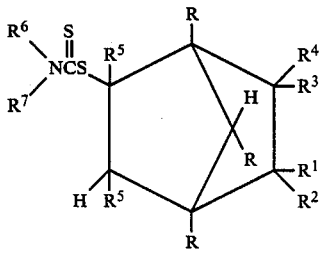
(A)

wherein:
- a. each of R, $R^2$ and $R^4$ when taken singly is a hydrogen atom, an alkyl group containing from 1 to about 15 carbon atoms, an aryl group containing from 6 to about 15 carbon atoms or a cycloalkyl group containing from 4 to about 10 carbon atoms;
- b. each of $R^1$ and $R^3$ when taken singly is a hydrogen atom, an alkyl group containing from 1 to about 15 carbon atoms; an aryl group containing from 6 to about 15 carbon atoms; a cycloalkyl group containing from 4 to about 10 carbon atoms or an alkenyl group containing from 2 to about 10 carbon atoms or $R^1$ and $R^3$ taken together form the group —CHYCY=CY— in which Y is a hydrogen atom or a methyl group or $R^1$ together with $R^2$ form an alkylidene group containing from 1 to about 6 carbon atoms;
- c. $R^5$ is a hydrogen atom or an alkyl group containing from 1 to about 15 carbon atoms;
- d. $R^6$ is an organic radical selected from an alkyl group, an alkenyl group, an aryl group or an aralkyl group in which the alkyl or alkenyl groups contain up to 32 carbon atoms and the aryl or aralkyl groups contain up to 15 carbon atoms each; and
- e. $R^7$ is hydrogen or an organic radical selected from an alkyl group or alkenyl group, an aryl or aralkyl group in which the alkyl or alkenyl groups contain up to 32 carbon atoms and the aryl or aralkyl groups contain up to 15 carbon atoms each.

The additives of the invention are readily prepared by reacting a primary or secondary amine, i.e. compounds having one or more primary or secondary amino groups, preferably primary and secondary monoamines of the general formula:

$R^6$—NH—$R^7$ where $R^6$ and $R^7$ are as defined above with carbon disulfide and a compound having the general formula:

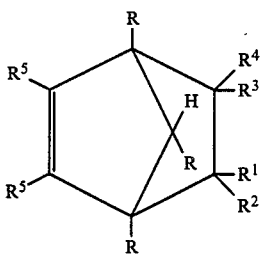
(B)

wherein R, $R^1$, $R^2$, $R^3$, $R^4$ and $R^5$ are as hereinbefore defined.

Specific examples of compound (B) which may be used in the practice of the present invention include 5-vinylnorbornene, dicyclopentadiene and norbornylene of which dicyclopentadiene and norbornylene are preferred.

As stated above, the amine reactants of the present invention can be represented by the formula:

$R^6$—NH—$R^7$ where $R^6$ is an organic radical, e.g. an alkyl group, an alkenyl group, an aryl group, or an aralkyl group. The alkyl or alkenyl groups can contain up to 32 carbon atoms, preferably up to 12 carbon atoms, and the aryl or aralkyl groups, which include a benzene or a naphthalene nucleus substituted by alkyl radicals or aryl or aralkyl radicals, preferably contain up to 15 carbon atoms each. The alkyl or alkenyl groups can be acyclic and of straight chain or branched structure, or they may be alicyclic. The $R^6$ group may be interrupted by a hetero atom linkage, such as O or S, and may contain one or more primary or secondary amino groups. In the foregoing formula, $R^7$ can be hydrogen, but it may be an alkyl, alkenyl, aryl or aralkyl group, as defined for $R^6$, and may be the same as $R^6$ or it may be different from $R^6$ in a given compound. When $R^6$ and $R^7$ are alkyl groups, they may be joined together to form a heterocyclic link with the nitrogen atom to which they are attached. $R^6$ and $R^7$ may also be substituted by non-interfering groups such as alkoxy, halo and amido groups, and the like.

Specific examples of suitable amine reactants which can be used in the practice of the present invention include methylamine, ethylamine, propylamine, isopropylamine, n-butylamine, sec-butylamine, isobutylamine, pentylamine, hexylamine, cyclohexylamine, heptylamine, octylamine, dodecylamine, octadecylamine, eicosylamine, triacontanylamine, benzylamine, chlorobenzylamine, nitrobenzylamine, 2-ethoxyethylamine, 4-carbomethoxyhexylamine, dimethylamine, diethylamine, di-n-propylamine, diisopropylamine, di-n-butylamine, di-sec-butylamine, diisobutylamine, di-tertbutylamine, dipentylamine, dihexylamine, dioctylamine, dieicosylamine, ditriacontanylamine, N-methylethylamine, N-methylpropylamine, N-methyloctadecylamine, N-ethylhexylamine, N-ethyldodecylamine, N-propyldodecylamine, aniline, toluidine (o-, m-, or p-), 2,4-xylidine, 3,4-xylidine, 2,5-xylidine, 4-ethylaniline, 3-propylaniline, 1,3-diamino benzene, 4,4'-diamino-diphenyl methane, p-chloro aniline, 2,6-diamino toluene, 4,4'-diaminodiphenyl, 2,4,4'-triamino diphenyl ether, 2,6-diamino naphthalene, 1,5-diamino-2-methylpentane, phenylethyl amine, piperidine, morpholine, piperazine, glycine, 2-amino ethyl ether, 2-amino ethyl sulfide, and the like. The referred amino compounds are lower alkyl secondary amines wherein each of $R^6$ and $R^7$ as described above have up to about 12 carbon atoms.

In the process of the invention, equal mole quantities of the reactants are used although a slight excess of carbon disulfide may be used, if desired, in order to compensate for any loss of carbon disulfide which can occur during the course of the reaction through volatilization to insure maximum yield of product. The reaction can be conveniently carried out by merely mixing the reactants and heating. However, it is preferably to add the amine reactant slowly, in a dropwise fashion, to a reaction vessel containing a mixture of the carbon disulfide and compound (B) reactants in order to avoid unwanted amine salt formation which can occur when all of the carbon disulfide reactant is contacted with all of the amine reactant simultaneously.

In general, a reaction temperature should be used which is high enough to promote the reaction at a reasonable rate, but not so high as to cause decomposition. A useful range is from about 30°–100° C. A more useful range is from about 50°–90° C.

The reaction can be carried out in an inert atmosphere if desired, but the use of an inert atmosphere above the reaction mixture is not required.

The reaction should be carried out for a time sufficient to form a substantial amount of product. This is usually accomplished from 0.5 to 12 hours. A more useful time range is from about 2 to 4 hours.

Thus, in accordance with another aspect of the invention, there is provided a process for preparing an oil-soluble compound having the formula:

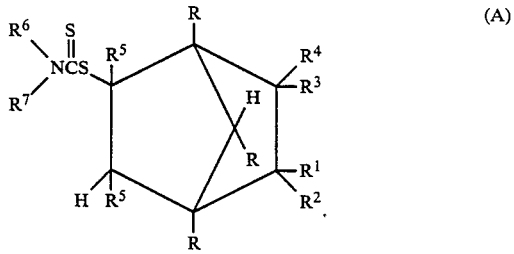

(A)

wherein:
a. each of R, $R^2$ and $R^4$ when taken singly is a hydrogen atom, an alkyl group containing from 1 to about 15 carbon atoms, an aryl group containing from 6 to about 15 carbon atoms or a cycloalkyl group containing from 4 to about 10 carbon atoms;
b. each of $R^1$ and $R^3$ when taken singly is a hydrogen atom, an alkyl group containing from 1 to about 15 carbon atoms; an aryl group containing from 6 to about 15 carbon atoms; a cycloalkyl group containing from 4 to about 10 carbon atoms or an alkenyl group containing from 2 to about 10 carbon atoms or $R^1$ and $R^3$ taken together form the group —CHYCY=CY— in which Y is a hydrogen atom or a methyl group or $R^1$ together with $R^2$ form an alkylidene group containing from 1 to about 6 carbon atoms;
c. $R^5$ is a hydrogen atom or an alkyl group containing from 1 to about 15 carbon atoms;
d. $R^6$ is an organic radical selected from an alkyl group, an alkenyl group, an aryl group or an aralkyl group in which the alkyl or alkenyl groups contain up to 32 carbon atoms and the aryl or aralkyl groups contain up to 15 carbon atoms each; and
e. $R^7$ is hydrogen or an organic radical selected from an alkyl group or alkenyl group, an aryl or aralkyl group in which the alkyl or alkenyl groups contain up to 32 carbon atoms and the aryl or aralkyl groups contain up to 15 carbon atoms each by reacting a compound having the general formula:

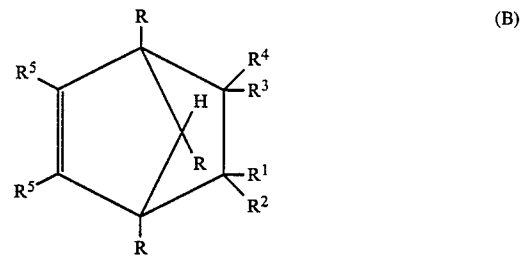

(B)

wherein R, $R^1$, $R^2$, $R^3$, $R^4$ and $R^5$ are as hereinbefore defined with carbon disulfide and an amine having the general formula:

$$R^6-NH-R^7$$

where $R^6$ is an organic radical selected from an alkyl group, an alkenyl group, an aryl group or an aralkyl group is which the alkyl or alkenyl groups contain up to 32 carbon atoms and the aryl or aralkyl groups contain up to 15 carbon atoms each; and, $R^7$ is hydrogen or an organic radical selected from an alkyl group or alkenyl group, an aryl or aralkyl group in which the alkyl or alkenyl groups contain up to 32 carbon atoms and the aryl or aralkyl groups contain up to 15 carbon atoms each.

Preferably, the lubricating compositions of the present invention comprise from 0.1% to 10%, more preferably, 0.25% to 5% by weight of the oil-soluble products of foregoing formula (A) and the lubricating oil may be any of the well-known mineral or synthetic oils of appropriate viscosity characteristics.

It will be understood that the lubricating compositions of the present invention may also contain, if desired, conventional lubricant additives such as ancillary antioxidants and antiwear additives (preferably ashless), corrosion inhibitors, dispersants, detergents, thickeners, pour-point depressants and viscosity index improvers.

Hence, in accordance with another aspect of the present invention there is provided a lubricating composition containing a major amount of lubricating oil and a minor antiwear-antioxidant amount of a compound having the general formula:

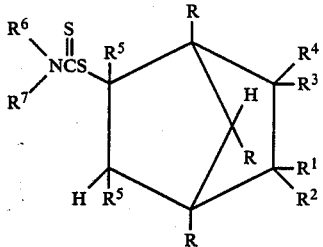

wherein:
a. each of R, $R^2$ and $R^4$ when taken singly is a hydrogen atom, an alkyl group containing from 1 to about 15 carbon atoms, an aryl group containing from 6 to about 15 carbon atoms or a cycloalkyl group containing from 4 to about 10 carbon atoms;
b. each of $R^1$ and $R^3$ when taken singly is a hydrogen atom, an alkyl group containing from 1 to about 15 carbon atoms; an aryl group containing from 6 to about 15 carbon atoms; a cycloalkyl group containing from 4 to about 10 carbon atoms or an alkenyl group containing from 2 to about 10 carbon atoms or $R^1$ and $R^3$ taken together form the group —CHYCY=CY— in which Y is a hydrogen atom or a methyl group or $R^1$ together with $R^2$ form an alkylidene group containing from 1 to about 6 carbon atoms;
c. $R^5$ is a hydrogen atom or an alkyl group containing from 1 to about 15 carbon atoms;
d. $R^6$ is an organic radical selected from an alkyl group, an alkenyl group, an aryl group or an aralkyl group in which the alkyl or alkenyl groups contain up to 32 carbon atoms and the aryl or aralkyl groups contain up to 15 carbon atoms each; and
e. $R^7$ is hydrogen or an organic radical selected from an alkyl group or alkenyl group, an aryl or aralkyl group in which the alkyl or alkenyl groups contain up to 32 carbon atoms and the aryl or aralkyl groups contain up to 15 carbon atoms each.

The additives of the present invention may also be conveniently prepared as a concentrate consisting of a concentrated solution of a major amount of the additives and a minor amount of a mineral or synthetic lubricating oil, or as an additive package consisting of a concentrated solution in mineral oil or synthetic oil of a major amount of a combination of the additives with one or more conventional additives. Such concentrates and packages are frequently very convenient forms in which to handle and transport additives and are diluted with further quantities of oil, and optionally blended with further additives, before use.

Thus, in accordance with a further aspect of the invention, there is provided a solution comprising a major amount of one or more compounds having the formula (A) and a minor amount of a lubricating oil. One or more conventional additives may be combined with the compounds of formula (A).

The following examples serve to illustrate the manner in which the antiwear and antioxidants additives are prepared but not to limit in any respect the scope of the invention claimed.

EXAMPLE I

To a 500 milliliter reaction vessel equipped with a stirrer, thermometer and condenser was added 37.6 grams (0.4 mole) of norbornylene and 38.0 grams (0.5 mole) of carbon disulfide and the mixture was heated gradually to 80° C. Beginning at 35° C., dibutylamine (51.6 grams; 0.4 mole) was added dropwise over a period of 30 minutes. After addition of the amine, the reaction mixture was maintained at 80° C. for 1.5 hours. Vacuum was applied for 30 minutes to strip off volatiles and the resulting product was dissolved in heptane and the heptane solution was washed twice with water, once with 10% aqueous sodium hydroxide, once with dilute hydrochloric acid and once again with water. The solvent was removed under vacuum after drying over anhydrous $Na_2SO_4$. A dark red liquid (95.6 grams) was obtained. Analysis by NMR served to identify the product as norbornyl dibutyldithiocarbamate.

EXAMPLE II

To a 500 milliliter reaction vessel equipped with a stirrer, thermometer and condenser was added 68.6 grams (0.52 mole) of dicyclopentadiene and 44.9 grams (0.59 mole) of carbon disulfide and the mixture was heated gently. At 38°–40° C., addition of dibutylamine was started. An exothermic reaction occurred and the temperature gradually rose to 90° C. Heating was stopped at 80° C. The addition of amine (62.1 grams; 0.52 mole) was completed in 45 minutes. The resulting mixture was held at 80° C. for one hour. Vacuum was then applied for 30 minutes to strip off volatiles. The resulting product was dissolved in heptane and the solution was washed once each with water, dilute hydrochloric acid, 5.0% aqueous sodium hydroxide, dilute hydrochloric acid and water. The heptane solution was then dried over anhydrous $Na_2SO_4$. After removal of solvent under vacuum there remained 141.8 grams of a dark orange liquid reaction product.

The antiwear properties of the lubricating oil compositions of the present invention were determined in a 4-Ball Wear Test. This test is conducted in a device comprising four steel balls, three of which are in contact with each other in one plane in a fixed triangular position and a reservoir containing the test sample. The fourth ball is above and in contact with the other three. In conducting the test, the upper ball is rotated while it is pressed against the other three balls while pressure is applied by weight and lever arms. The diameter of the scar on the three lower balls is measured by means of a low-power microscope, and the average diameter measured in two directions on each of three lower balls is taken as a measure of the antiwear characteristics of the oil. A larger scar diameter means more wear. The balls were immersed in base lube oil containing the test additives. Applied load was 40 kg and rotation was at 1800 rpm for 30 minutes at 130° F. Tests conducted with base oil alone (Exxon 80W-90 mineral oil) and with base oil containing 0.5 wt. % of the additives of Examples I and II. Results are given in the following table.

| Oil Formulation | Scar Diameter (mm) |
| --- | --- |
| Base Oil | 0.663 |
| Base Oil + 0.5 wt. % additive (Example I) | 0.483 |
| Base Oil + 0.5 wt. % additive (Example II) | 0.500 |

The results in the table show that lubricating oil containing the additives of the present invention gave a scar diameter significantly less than that of the base oil alone.

Hot Oil Oxidation Test were carried out to demonstrate the antioxidant effectiveness of the present additives. In these tests, fully formulated mineral lubricating oil samples were prepared both with and without the additive. The oil is placed in a test cell together with 0.3 cubic centimeter of a catalyst composition prepared by dissolving 6.65 grams of ferric acetylacetonate and 0.6 gram of cupric acetylacetonate in 100 grams of xylene. This cell was heated to 160° C. and dry air blown through the heated oil for 48 hours at a rate of 10 liters/hour. The percent viscosity increase was measured at 40° C. The following results were obtained:

| Additive | Percent Viscosity Increase |
|---|---|
| None | 64.7 |
| Example I (0.26 wt. % based on total weight of the oil) | 30.7 |
| Example II (0.26 wt. % based on total weight of the oil) | 35.0 |

These results demonstrate that the additive compounds of the invention are effective antioxidants.

What is claimed:

1. Compounds having the formula:

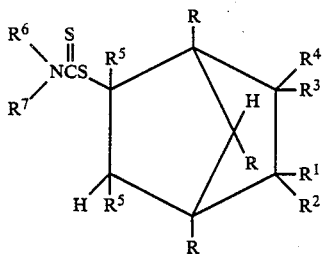

(A)

wherein:
a. each of R, $R^2$ and $R^4$ when taken singly is a hydrogen atom, an alkyl group containing from 1 to 15 carbon atoms, an aryl group consisting of a benzene or a naphthalene group containing from 6 to 15 carbon atoms or a cycloalkyl group containing from 4 to 10 carbon atoms;
b. each of $R^1$ and $R^3$ when taken singly is a hydrogen atom, an alkyl group containing from 1 to 15 carbon atoms; an aryl group consisting of a benzene or a naphthalene group containing from 6 to 15 carbon atoms; a cycloalkyl group containing from 4 to 10 carbon atoms or an alkenyl group containing from 2 to 10 carbon atoms or $R^1$ or $R^3$ taken together form the group —CHYCY=CY— in which Y is a hydrogen atom or a methyl group or $R^1$ together with $R^2$ form an alkylidene group containing from 1 to 6 carbon atoms;
c. $R^5$ is a hydrogen atom or an alkyl group containing from 1 to 15 carbon atoms;
d. $R^6$ is an organic radical selected from an alkyl group, an alkenyl group, an aryl group or an aralkyl group in which the alkyl or alkenyl groups contain up to 32 carbon atoms and the aryl or aralkyl groups are selected from benzene and naphthalene groups which contain up to 15 carbon atoms each; and
e. $R^7$ hydrogen or an organic radical selected from an alkyl group or alkenyl group, an aryl or aralkyl group in which the alkyl or alkenyl groups contain up to 32 carbon atoms and the aryl or aralkyl groups are selected from benzene and naphthalene groups which contain up to 15 carbon atoms each.

2. The compound of claim 1 wherein $R^6$ and $R^7$ are n-butyl and R, $R^1$, $R^2$, $R^3$, $R^4$ and $R^5$ are hydrogen.

3. The compound of claim 1 wherein $R^6$ and $R^7$ are n-butyl, R, $R^2$, $R^4$ and $R^5$ are hydrogen and $R^1$ and $R^3$ taken together form the group —$CH_2CH=CH$—.

4. The compound of claim 1 wherein $R^6$ and $R^7$ are isopropyl, R, $R^1$, $R^2$, $R^4$ and $R^5$ are hydrogen and $R^3$ is —$CH=CH_2$.

* * * * *